United States Patent [19]
Lovitt

[11] Patent Number: 4,890,340
[45] Date of Patent: Jan. 2, 1990

[54] SELF-CONTAINED HAND-HELD BIDET

[76] Inventor: Harold B. Lovitt, 8427 Kirkwood Dr., Los Angeles, Calif. 90046

[21] Appl. No.: 249,053

[22] Filed: Sep. 26, 1988

[51] Int. Cl.[4] ............................................. A61H 35/00
[52] U.S. Cl. ........................................... 4/443; 4/448; 128/66
[58] Field of Search .................. 4/420, 420.1, 420.2, 4/420.3, 420.4, 420.5, 443, 444, 445, 446, 477, 448; D23/295, 299; D24/60; 128/66, 200.14–200.23; 604/279, 58, 60, 217, 218, 212, 185, 37, 39, 41, 240

[56] References Cited

U.S. PATENT DOCUMENTS

| | | | |
|---|---|---|---|
| 643,867 | 2/1900 | De Vilbiss | 604/58 |
| 3,148,806 | 9/1964 | Meshberg | 128/200.23 |
| 3,653,377 | 4/1972 | Rebold | 128/66 |
| 3,731,676 | 5/1973 | Rebold | 128/66 |
| 3,783,867 | 1/1974 | Summersby et al. | 128/66 |
| 3,808,608 | 5/1974 | Caplan | 4/448 |
| 3,874,381 | 4/1975 | Baum | 128/200.14 |
| 3,914,804 | 10/1975 | Schrader et al. | 4/420.2 |
| 4,000,742 | 1/1977 | DiGlacomo | 4/448 |
| 4,014,355 | 3/1977 | DiMatteo et al. | 4/420.2 |
| 4,069,519 | 1/1978 | Alexander | 4/447 |
| 4,069,520 | 1/1978 | Thomas | 4/446 |
| 4,178,931 | 12/1979 | Lind et al. | 4/448 |
| 4,206,520 | 6/1980 | Fulford | 4/665 |
| 4,422,189 | 12/1983 | Couvrette | 4/420.2 |
| 4,456,007 | 6/1984 | Nakao et al. | 128/200.21 |
| 4,510,630 | 4/1985 | Osgood | 4/443 |
| 4,622,704 | 11/1986 | Chung | 4/443 |

FOREIGN PATENT DOCUMENTS

| | | | |
|---|---|---|---|
| 477520 | 12/1929 | Fed. Rep. of Germany | 4/443 |
| 4019 | of 1891 | United Kingdom | 4/447 |
| 1535794 | 12/1978 | United Kingdom | 4/448 |

Primary Examiner—Henry J. Recla
Assistant Examiner—Edward C. Donovan
Attorney, Agent, or Firm—Nilsson, Robbins, Dalgarn, Berliner, Carson & Wurst

[57] ABSTRACT

A self-contained hand-held bidet device, for providing lavaging action with portability and convenience. The device comprises a housing having a motorized pump with a power source and switch for activating the pump. The pump draws fluid from a reservoir mounted at one end of the housing and pumps the fluid through a pivotal conduit to exit as a spray. Lightweight construction, a collapsible reservoir and the pivotally mounted wand facilitate convenient storage.

10 Claims, 2 Drawing Sheets

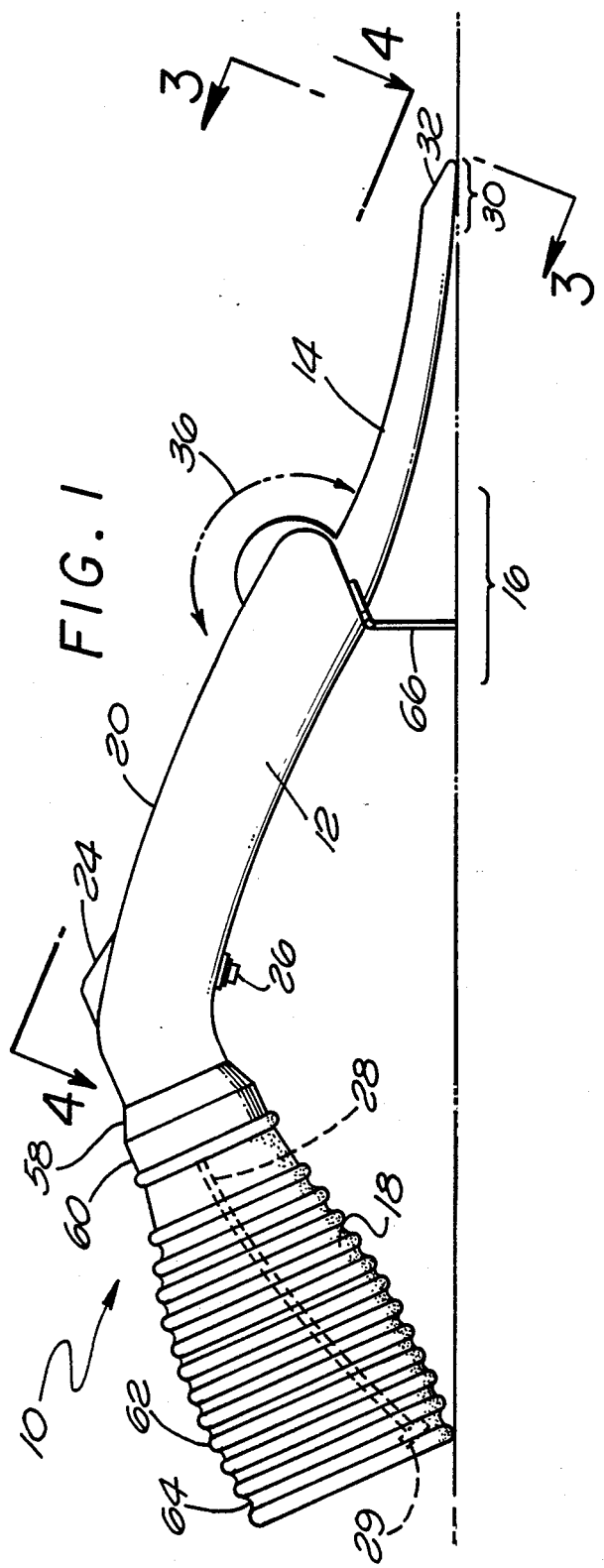
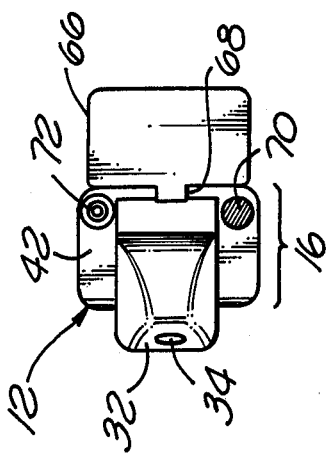
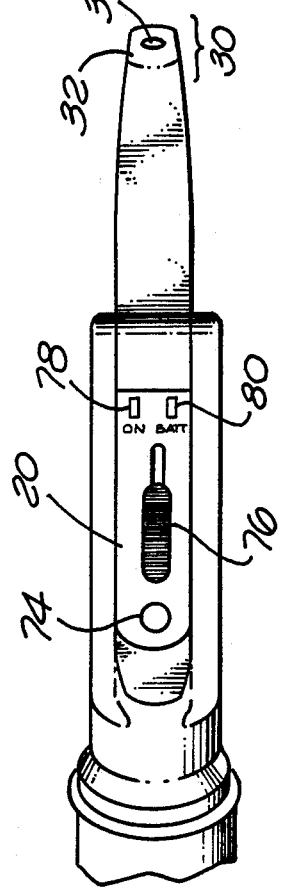

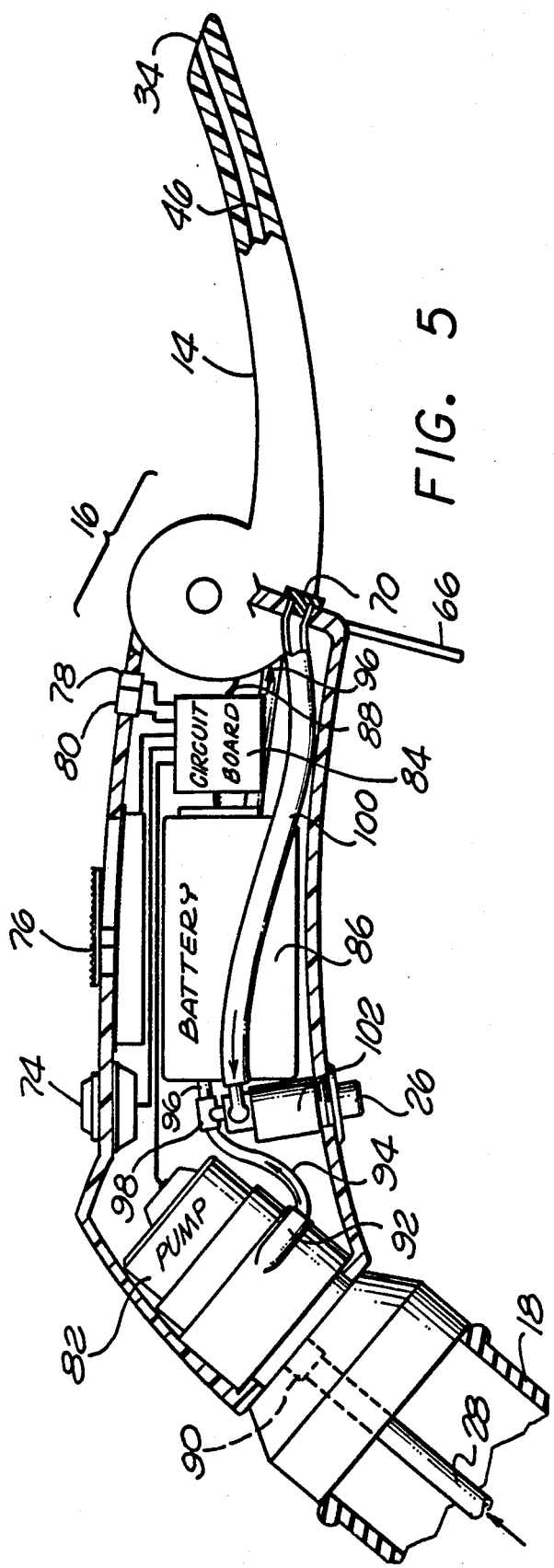
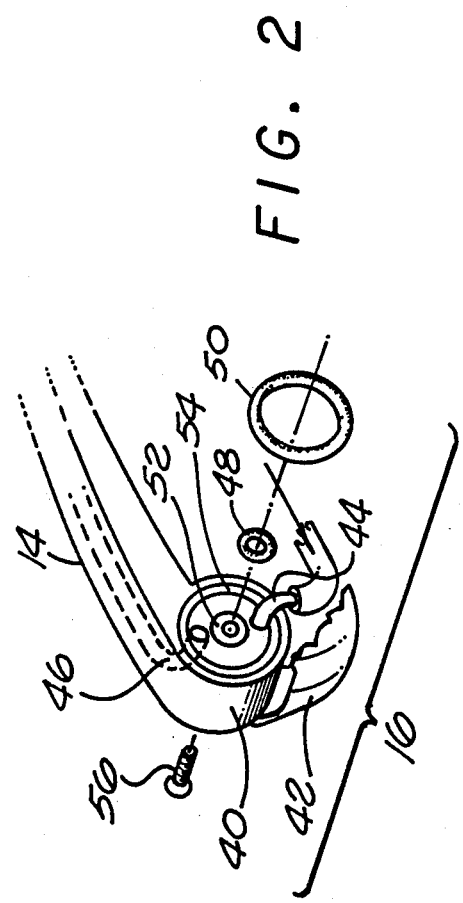

SELF-CONTAINED HAND-HELD BIDET

BACKGROUND OF THE INVENTION

The present invention relates in general to the field of hygienic devices and in particular to bidets. In that regard, the present invention is a portable, hand-held bidet for effective, hygienic cleaning with comfort and convenience.

Traditionally, bidets perform various sanitary functions as in cleansing a soiled body area after voiding, and often accomplish this function to a degree superior to conventional sanitary devices. A conventional bidet is a rather large, non-portable fixture with attached plumbing to provide water supply and drainage. To use a conventional bidet, a user sits or crouches over the bidet so that the desired body area will be cleansed. The user then operates a knob causing water to be sprayed on a body area.

The lavaging action of a conventional bidet is particularly quick, efficient and beneficial to persons who suffer from various medical problems, for example, hemorrhoids and genital or rectal infections. For these persons, there is a significant measure of discomfort attendant using other conventional sanitary devices, e.g. toilet paper and conventional flush toilets. In some cases, these other conventional devices cannot be used at all. These problems are complicated by the fact that in many areas, bidets are not common. Thus, persons who would benefit from use of a conventional bidet may find their quality of life lessened by the inconvenience, discomfort and health risks of being unable to readily avail themselves of a bidet when the need arises.

In response to these problems, various attachment apparatuses have been proposed for mounting on a conventional flush toilet. Examples of such apparatuses are described in Kawai et al., U.S. Pat. No. 4,411,030; Matsui et al., U.S. Pat. No. 4,581,779; and Schrader et al., U.S. Pat. No. 3,914,804. Essentially, these structures are rather bulky, non-portable adaptor fixtures limited to one location.

The limited accessibility of non-portable and bulky conventional bidets or bidet attachment structures have put many bidet users at some inconvenience and prevented other potential users from obtaining the benefits of a bidet. Thus, the problems of inaccessibility, non-portability and the expense of conventional bidets restrict many persons from the benefits and convenience a bidet provides.

Accordingly, a substantial need exists for a relatively inexpensive, portable, easy-to-use bidet. In this regard, the present invention is directed to a self-contained, hand-held bidet of relatively compact size, that is easy to use and provides the full benefits of a traditional bidet as well as other benefits. The present invention also provides the user with a measure of convenience not attendant traditional, conventional bidet apparatuses. The present invention comprises a housing molded into a comfortable, easy-to-hold shape and containing a power source, water pump and an on/off switch. At one end of the housing a fluid reservoir is removably attached. At the other end of the housing a conduit having a nozzle end is pivotally mounted for directing a spray of water.

BRIEF DESCRIPTION OF THE DRAWINGS

FIG. 1 is a side elevation view of the device of the present invention;

FIG. 2 is a fragmentary perspective view of a component of the device of FIG. 1;

FIG. 3 is an end view taken along the line 3—3 of FIG. 2;

FIG. 4 is a partial top view taken along the line 4—4 of FIG. 1; and

FIG. 5 is vertical cross-sectional, view of the device in FIG. 1.

DESCRIPTION OF THE ILLUSTRATIVE EMBODIMENT

A detailed illustrative embodiment of the present invention is disclosed herein; however, it is merely representative recognizing that various electrical and mechanical components and various structural elements may be embodied in a wide variety of forms, some of which may be quite different from those specific structural and functional details disclosed herein. Consequently, the details disclosed herein are merely representative, yet in that regard they are deemed to afford the best embodiment for the purposes of disclosure to provide a basis for the claims herein which define the scope of the present invention.

Referring initially to FIG. 1, there is illustrated a self-contained, hand-held bidet unit 10 in accordance with the present invention. A housing 12, made of plastic, fiberglass or lightweight metal and having a contoured, curved shape, is connected at one end to a conduit 14 by a pivot joint 16 and, at its other end, is coupled to a collapsible fluid reservoir 18. The housing 12 is substantially cylindrical in circumference and is curved throughout its length. The contoured, curved design of the housing 12 is designed to fit comfortably in either hand for easy manipulation and use of the unit 10. In this regard, the housing 12 has a flattened area corresponding to a control panel 18 (FIG. 4), a contoured support structure corresponding to a hand or thumb rest 24 (FIG. 1) and various other operational features such as a soap/medication dispenser button 26 that protrude from the housing 12. The relatively compact size and contoured shape of the housing 12 and convenient positioning of both control panel 20 and soap/medication button 26 enable a user to operate the unit 10 with one hand.

As shown in FIG. 1, the curvature of the housing 12 is accentuated near the reservoir 18. Consequently, the overall shape of the unit 10 is somewhat bent or angular. This design has several advantages. For example, when the unit 10 is operated in the position shown in FIG. 1, substantially all of the fluid contained within the fluid reservoir 18 can be drawn from it by means of an intake tube 28 shown in dotted lines. In this regard, the intake tube 28 has a screen filter 29 mounted to its intake end and extends to substantially the lowest region of the fluid reservoir 18 thereby maximizing the volume of fluid which may be drawn from the fluid reservoir 18.

Similarly, the unit's angular shape serves to balance the unit 10, thereby contributing to its easy manipulation and use. In this regard, the mass of filled fluid reservoir 18 is somewhat counterbalanced by the mass of the housing 12, its components and the extended conduit 14. Accordingly, relatively little effort is required by the user to hold, operate and control the unit 10 in the operational position shown in FIG. 1.

The conduit 14, made of plastic or light metal, is pivotally mounted to the housing 12 and has a nozzle end 30 having a beveled surface 32 that defines a nozzle orifice 34 (FIG. 4) from which sprayed fluid exits the conduit 14. As shown by an arcuate arrow 36 (FIG. 1), the pivotal mounting of the conduit 14 allows it to be extended for spraying by pivoting it to an "open" position in which the unit 10 is operated (shown in FIG. 1). For storage, the conduit 14 is folded by pivoting to a "closed" position for convenient storage and portability of the unit 10. When not in use, the unit 10 may be rested on a surface supported by the fluid reservoir 18 and a protective plate that otherwise may be flipped closed to cover the end of the unit 10.

Referring briefly to FIG. 2, the structure and operation of the pivot joint 16 (FIG. 1) will now be described. The ball and socket arrangement of the pivot joint 16 is comprised of a ball end 40 of the conduit 14 which is pivotally mated into a "U" shaped socket structure 42 formed by the end of the housing 12. The end view illustrated in FIG. 2 more clearly shows the design of "U" shaped socket structure 42 into which the ball end 40 fits. The pivot joint 16 enables the conduit 14 to be easily opened and closed. During operation of the unit 10, the pivot joint 16 maintains a substantially leak-tight seal between the output end of output tube 44 located in the housing 12 and the intake end of the tubular bore 46 formed by the conduit 14. The leak-tight seal at the pivot joint 16 between these two tubular, fluid-bearing elements is accomplished by a system of concentrically seated O-rings 48 and 50 that rest in concentric channels 52 and 54 located on either or both the ball end 40 and the socket structure 42 and held in connective engagement via screw 56.

The conduit 14 is rotatable around the axis centered at the screw 56 which serves as the axle for the pivot joint 16. As illustrated in FIG. 2, the pivot joint 16 is shown with the conduit 14 in the closed position with the output end of the output tube 44 and intake end of tubular bore 46 being unaligned which prevents fluid from traveling through the pivot joint 16. However, when the conduit 14 is pivoted into the open position, the output end of the output tube 44 is aligned with the intake end of the tubular bore 46 to provide a substantially continuous flow path for fluid pumped through the pivot joint 16.

Referring now to FIGS. 1 and 4, the slightly tapered, curved shape of the conduit 14 assists the user in directing a stream of fluid to the desired body area without having to assume unnatural or uncomfortable body or arm positions. For example, in the working embodiment shown in FIG. 1, the curved shape of the conduit 14 would extend somewhat downwardly between the legs and near the user's genital area to enable the user to comfortably direct a stream of fluid to the genital area while in a sitting position. Since the conduit 14 is relatively narrow and tapered from the ball end 40 to the nozzle end 30, as illustrated in FIG. 4, it may be easily positioned between and slightly beneath the user's legs. Accordingly, this tapered design enables the unit 10 to be comfortably and easily used by many persons without significant effort. Similarly, the length of the conduit 14 allows the user, while in a sitting position, to reach their genital area with a cleansing stream of fluid with relative ease.

As illustrated in FIGS. 1 and 3, one end of the conduit 14 forms the nozzle end 30 which is designed to spray a single, coherent stream of fluid from the nozzle orifice 34 substantially orthogonal to the beveled surface 32. Accordingly, during use of the unit 10 the stream of fluid is directed to the desired area but sufficiently away from the conduit 14 and nozzle end 30 and substantially prevents soiling or contaminating material from the lavaged area from coming into contact with any part of the unit 10.

Referring again to FIG. 1, the coupling, made of light metal or plastic, couples the fluid reservoir 18 to the rest of the unit 10. The coupling has a truncated conical section 58 which forms a transitional structure between the housing 12 and a mating ring 60 which has a larger diameter. Both the inner wall (not shown) of the mating ring 60 and the outer wall of the mouth (not shown) of the fluid reservoir 18 are threaded so that the fluid reservoir 18 may be threadably secured.

The fluid reservoir 18, made of plastic or rubber, is collapsible for convenient storage and portability. In this regard, the fluid reservoir 18 incorporates an accordion-like design in its structure. Accordingly, alternating ridges 62 and valleys 64 extend circumferentially over a substantial portion of the fluid reservoir 18. In use, the fluid reservoir 18 may be expanded to its maximum fluid capacity. After use, the fluid reservoir 18 can be transformed into a compact, cylindrical shape by collapsing it thereby compressing the alternating ridges 62 and valleys 64 together in an accordion-like fashion. The ready and easy collapsibility of the fluid reservoir results in substantial space savings for storage and portability of the unit 10.

The fluid reservoir 18 is capable of holding enough fluid that the bidet may adequately lavage the desired area. In this regard, various volumetric capacities for the fluid reservoir 18 are possible. However, for use of unit 10 as a bidet, a volume of approximately one-half liter has been found to be sufficient for providing adequate lavaging. Additionally, it should be noted that the fluid reservoir 18, and indeed the unit 10, may be used with a wide variety of fluids, including water or medicated solutions, depending on the user's needs.

Referring to FIG. 3, when the unit 10 is in the "open" position, a protective plate 66 flips down via a spring-loaded hinge 68 to provide a support for resting the unit 10 on a surface and, at the same time, to provide access to other features of the unit 10. In the "closed" position, the protective plate 66 protects the end of the unit 10 and is held closed by the spring-loaded hinge 68 to prevent it from opening accidentally. Flipping down plate 66 exposes a soap/medicant reservoir access plug 70 and a battery recharging socket 72. Since the protective plate 66 can be opened independently of pivoting the conduit 14 into the open position, soap or medication may be added to the unit 10 by removing access plug 70 and filling that reservoir without pivoting the conduit 14 to the open position. Similarly, recharging of the unit's batteries may be accomplished by attaching an appropriate adaptor/recharger unit to the batter recharging socket 72.

Referring now to FIG. 4, some discussion of the control features of the present invention are appropriate. FIG. 4 is a partial top view of the device in FIG. 1 that illustrates an exemplary control panel 20 of the unit 10. The control panel 20 comprises the flattened upper surface of the housing 12 when the unit 10 is in the "closed" position, i.e. when conduit 14 is pivoted to rest against the control panel 20. To access the control panel 20 and operate the unit 10, the user pivots the conduit 14 to the open position, thereby exposing the control panel 20. Located on the control panel 20 is an on/off switch 74, rheostat 76, an "on/off" indicator light 78 and a "battery low" indicator light 80. The on/off switch 74 enables the user to switch the unit 10 on or off. When the unit 10 is on, the "on/off" indicator light 78 is illuminated to provide the user with a visual indication. The rheostat 76 enables the user to vary the pressure of the stream of fluid by controlling the output of a pump located within the housing 12. If the unit 10 needs recharging or needs a new battery, then the "battery low" indicator light 80 is illuminated when the unit 10 is activated.

Referring now to FIG. 5, the further specifics regarding the structure and operation of the present invention will be described in more detail. Positioned in the housing 12 are, among other things, an electric system comprising the on/off switch 74, rheostat switch 76, "on/off" indicator light 78, "battery low" indicator light 80 and pump 82 each of which is wired to a circuit board 84 which is in turn wired to a battery 86 for powering the unit 10. If a rechargeable battery is utilized to power the unit 10, then the circuit board 84 is additionally wired to the battery recharging socket 72 (FIG. 3) via a connection 88.

In operation, the unit 10 is switched on by depressing the on/off switch 74 which energizes unit 10, both illuminating on/off indicator light 78 and energizing the pump 82. When the user moves rheostat 76, the pump 82 is activated to operate at the speed selected by the user via the rheostat 76. Accordingly, the pump 82 draws fluid from the reservoir 18 via intake tube 28 and into the pump 82 through a pump intake port 90. The fluid is then driven from the pump 82 through a pump output port 92 through an output tube 94 to a secondary output tube 96 via "T" junction 98. The secondary output tube 96 supplies fluid to the conduit 14 through pivot joint 16. The fluid travels through the tubular bore 46 of the conduit 14 and exits the unit 10 through the nozzle orifice 34 as a spray or stream for lavaging.

To use the present invention, the user first removes and fills the fluid reservoir 18 with fluid. Lukewarm water is usually preferred by most bidet users, but other fluids may be used depending on the user's needs. Once filled, the fluid reservoir 18 is reattached via coupling 20 to the housing 12. The user then pivots the conduit 14 to the open position to extend the nozzle end 30 to a spraying position and to expose the control panel 20. Subsequently, the user assumes a comfortable position, e.g. sitting or crouching position usually on or over a receptacle such as a conventional flush toilet bowl, and positions the unit 10 so that the spray from the nozzle orifice 34 will impact on the desired body area.

When ready, the user activates the unit 10 by depressing the on/off switch 74 to the "on" position which energizes the unit 10 as indicated by illuminating the "on/off" indicator light 78. The user then slides the rheostat 76 to adjust the pressure of the spray and lavages their genital area until it is cleansed or until the fluid supply in the fluid reservoir 18 is exhausted. As noted earlier, the design of the unit 10 substantially reduces the opportunity for contamination of the unit 10 by contact with contaminated matter or fluid from the sprayed area. Once finished, the user depresses the "on/off" switch 74 to return it to the off position thereby deactivating the unit 10 and extinguishing "on/off" indicator light 78.

If further lavaging is desired, the reservoir 18 may be removed, refilled and reattached and the unit 10 reactivated. This cycle may be repeated as many times as desired. However, for normal use, the volume of fluid in reservoir 18 is usually sufficient to provide adequate cleaning action within one cycle. When the user finishes with their ablutions, they deactivate the unit 10 and prepare it for storage by pivoting the conduit 14 into the closed position and flip plate 66 into the up position to cover that end of the housing 12. The reservoir 18 may be removed, rinsed, dried and collapsed and the whole unit 10 stored conveniently in a purse or handy carrying case for easy portability until needed again.

Various modifications of the present invention may enhance its utility and effectiveness. For example, referring to FIG. 5, the present invention may also be used to apply soap or medication together with the stream of fluid to enhance the cleansing action and medical uses of the unit 10. In this regard, a soap/medication reservoir 100 and dispenser 102 are provided for injecting soap or medication into the stream of fluid during the bidet's operation. To utilize this feature, the user simply removes access plug 70 from the end of the reservoir 100 and fills it with soap or medication and reseals the reservoir 100 by replacing access plug 70. The user then activates the bidet 10 as described earlier and, while lavaging, depresses a button 26 (FIG. 1) on the dispenser 100 thereby causing a small amount of soap or medication to be injected into the stream of fluid at the "T" junction 98. Repeated depressing of the button 26 enables the unit 10 to deliver several applications of soap or medicated solution onto the desired body area.

The portability of the present invention and its compact design enables a user to obtain the traditional benefits of a bidet almost anywhere, whenever the need for use arises. In this regard, a collapsible reservoir and pivotally mounted conduit contribute to the compact size of the present invention, enabling it to be carried in a purse or in its own convenient carrying case. Because the present invention is a self-contained unit, its convenience is further enhanced. In this regard, the present invention provides its own fluid source, i.e. fluid reservoir 18 (FIG. 1) and its own power source, i.e. battery 86 (FIG. 4).

The present invention is easy and convenient for almost anyone to use as a bidet. However, the present invention is suitable for other uses, for example, as a bathing device for bedridden patients or babies. In this regard, the present invention may be used in a variety of ways for a variety of purposes including as a bidet, a bathing apparatus, a medication applicator and as a therapeutic device. Thus, health professionals, such as physicians and nurses, might utilize the present invention as a convenient, safe, easy-to-use means for providing enhanced patient care.

In view of the above description of the preferred embodiment, it will be apparent that the present invention is capable of economical implementation in a variety of shapes and functional designs to accomplish an effective, economical and easy-to-use bidet. Such modifications may include varying the reservoir capacity, increasing or decreasing the pump rate or the type of pump used, and varying the spray patterns produced by the nozzle to effectively address the needs of the user and contemplated use of the present invention. Consequently, the scope of the present invention hereof is deemed to be appropriately determined by the claims as set forth below.

What is claimed is:

1. A self-contained hand-held bidet device for discharging a stream of fluid comprising:
   a rigid elongate slender housing adapted to be held in the hand of a user defining an internal space between first and second ends;
   a nozzle means defining an elongate conduit to carry and direct said stream of fluid;
   a fluid-seal pivot means rigidly affixing said nozzle means to said first end of said housing, said nozzle means accordingly being mounted to move between extended and retracted positions relative to said housing said pivot means and said nozzle means, when in the extended position, being sized and shaped to spray said stream of fluid away from said conduit toward its longitudinal direction to impact said genital area of said user;
   a reservoir means for receiving said fluid, said reservoir means being attached to said second end of said housing; and
   pump means affixed in said internal space of said housing for drawing fluid from said reservoir means and forcing a fluid stream through said fluid seal pivot means to emerge from said nozzle means.

2. A bidet device according to claim 1 wherein said nozzle means comprises an elongate arcuate conduit and said housing defines an aligned surface to mate with a surface of said conduit in said retracted position.

3. A bidet device according to claim 1 wherein said pump means includes an electric pump, a control circuit, a switch and battery means.

4. A bidet device according to claim 1 wherein said reservoir means comprises an accordion-like structure collapsible to a reduced size.

5. A bidet device according to claim 1 wherein said reservoir means comprises a removably attached structure, removable from said housing to be filled with fluid.

6. A bidet device according to claim 1 wherein said reservoir is expandable to accommodate substantially one-half liter of fluid.

7. A bidet device according to claim 1 further including a soap/medication chamber and means for connecting said chamber to said pump means to inject soap/medication.

8. A bidet device according to claim 1 wherein said pivot means includes a cylindrical structure defining an axially parallel passage for said fluid.

9. A bidet device according to claim 1 wherein said pivot means mounts said nozzle means to swing between said extended and retracted positions.

10. A bidet device according to claim 1 wherein said housing defines a handle for said device.

* * * * *